United States Patent
Cha et al.

(10) Patent No.: US 7,387,609 B2
(45) Date of Patent: Jun. 17, 2008

(54) METHOD OF MEASURING ABSOLUTE LUNG VOLUME BASED ON $O_2/CO_2$ GAS ANALYSIS

(76) Inventors: Eun Jong Cha, Jukong Apt. 208-205, Mochung-Dong, Heungdeok-Gu, Cheongju-City, Chungcheongbuk-Do (KR); Shin Won Kang, Manchon-woobang 2cha Town, 207-1002, Manchon-Dong, Suseong-Gu, Daegu-City (KR); Kyung Ah Kim, Dukhee Apt. 1207, Sajik 2-Dong, Heungdeok-Gu, Cheongji-City, Chungcheongbuk-Do (KR)

( * ) Notice: Subject to any disclaimer, the term of this patent is extended or adjusted under 35 U.S.C. 154(b) by 418 days.

(21) Appl. No.: 11/017,852

(22) Filed: Dec. 22, 2004

(65) Prior Publication Data
US 2006/0096591 A1 May 11, 2006

(30) Foreign Application Priority Data
Nov. 11, 2004 (KR) .................. 10-2004-0092035

(51) Int. Cl.
*A61B 5/02* (2006.01)
(52) U.S. Cl. ........................ 600/532; 600/529
(58) Field of Classification Search .............. None
See application file for complete search history.

(56) References Cited

U.S. PATENT DOCUMENTS 6,544,191 B2 * 4/2003 Koch et al. .................. 600/538
6,575,918 B2 * 6/2003 Kline ........................ 600/532

* cited by examiner

Primary Examiner—Robert L Nasser
(74) Attorney, Agent, or Firm—Birch, Stewart, Kolasch & Birch, LLP

(57) ABSTRACT

Disclosed herein is a method of measuring an absolute lung volume. In the method, concentrations of oxygen and carbon dioxide gases are measured and analyzed in respiratory gas, consisting of nitrogen ($N_2$), oxygen ($O_2$), and carbon dioxide ($CO_2$), to indirectly measure a concentration of nitrogen, thereby achieving measurement of absolute lung volume, such as a functional residual capacity. The method comprises connecting a one-way valve to a subject so as to separate an inspiration path from an expiration path, measuring a flow rate of respiratory gas using a flow sensor, which is provided in the expiration path, continuously measuring a concentration ($F_{O2}$) of oxygen and a concentration ($F_{CO2}$) of carbon dioxide using $O_2$ and $CO_2$ sensors provided in the expiration path, correcting dynamic characteristics of the concentration ($F_{O2}$) of oxygen and the concentration ($F_{CO2}$) of carbon dioxide so that the dynamic characteristics agree with each other in terms of time, and analyzing oxygen and carbon dioxide gases using the following Equation $$FRC = \frac{1}{0.79} \int (1 - (F_{O2} - F_{CO2}))F dt.$$

4 Claims, 7 Drawing Sheets

METHOD OF MEASURING ABSOLUTE LUNG VOLUME BASED ON $O_2/CO_2$ GAS ANALYSIS

BACKGROUND OF THE INVENTION

1. Field of the Invention

The present invention relates, in general, to a method of measuring an absolute lung volume based on $O_2/CO_2$ gas analysis and, more particularly, to a method of measuring an absolute lung volume based on $O_2/CO_2$ gas analysis, in which concentrations of oxygen and carbon dioxide gases are measured and analyzed in respiratory gas, consisting of nitrogen ($N_2$), oxygen ($O_2$), and carbon dioxide ($CO_2$), to indirectly measure a concentration of nitrogen, thereby achieving measurement of the absolute lung volume, including a functional residual capacity.

2. Description of the Related Art

Exhaled through expiration during respiration of humans, respiratory gas consists of only nitrogen ($N_2$), oxygen ($O_2$), and carbon dioxide ($CO_2$). A concentration of the respiratory gas exhaled during the respiration of humans is important to evaluate a respiratory function. For example, the evaluation of the respiratory function is implemented in such a way that expired air, which is generated through a physiological gas exchange process in the lung after inspiring 100% oxygen, is collected and subjected to concentration analysis so as to measure, for example, concentrations of oxygen, carbon dioxide, and nitrogen. Used to evaluate the respiratory function, an absolute lung volume, such as a functional residual capacity (hereinafter, referred to as "FRC"), is a very important parameter for diagnosing a chronic respiratory disease.

The FRC denotes a volume of air remaining in the lung at the moment that expiration ends, and is normally about 1-2 L. Of methods of measuring the FRC, a whole-body plethysmography is the most precise method. However, the whole-body plethysmography is disadvantageous in that a volume of air existing in the abdominal cavity is included in measurements, and that it is impossible to apply to claustrophobia patients or patients who have difficulty in breathing because a subject must respire in a closed large box.

Accordingly, an $N_2$ wash-out test is clinically used to measure the FRC. The $N_2$ wash-out test employs the property that nitrogen does not diffuse into a closed capillary. As shown in FIG. 1, in the $N_2$ wash-out test, a three-way valve 50 is connected to a subject 40, who inspires air, to form an air feeding path 13, and an inspiration path 11 and an expiration path 12 of the subject. The inspiration path 11 and the expiration path 12 of the subject 40 are divided by one-way valves 10, 20, and an airbag 30 is connected to the expiration path 12 to collect expired gases.

When the subject 40, who respires air fed through the air feeding path 13, is in an FRC state, that is, when the subject 40 is in the last stage of expiration, the lung of the subject 40 is fully filled with air and a concentration of nitrogen is 79% in the air. Hence, the total nitrogen volume ($V_{N2}$) of the lung of the subject is 0.79×FRC as shown in Equation 1.

$$V_{N2} = 0.79 \times FRC \qquad \text{Formula 1}$$

At this stage, the three-way valve 50 is adjusted to allow the subject to inspire 100% oxygen fed through the inspiration path 11, and expired gas is collected through the expiration path 12 in the airbag 30. When 100% oxygen is inspired through the inspiration path 13, air in the lung of the subject 40 is diluted by oxygen fed into the lung. If the subject expires the air, which is diluted by oxygen, from the lung, the concentration of nitrogen in the expired gas is reduced to be less than 79% of the initial concentration. Upon repeating this process, the lung of the subject 40 is fully filled with oxygen, and the concentration of nitrogen in the expired gas becomes 0%.

In the FRC state in which the lung of the subject is fully filled with air containing 79% nitrogen, the inspiration of 100% oxygen is repeated to collect the expired gas in the airbag 30 until the concentration of nitrogen is 0% in the expired gas, thereby completely transferring nitrogen from the lung of the subject 40 into the airbag.

Calculated using a volume ($V_B$) of the airbag and a nitrogen concentration ratio ($F_{N2}$) of gas in the airbag, a volume ($V_{N2}$) of nitrogen in the airbag 30 is $V_B \times F_{N2}$ as shown in Equation 2.

$$V_{N2} = F_{N2} V_B \qquad \text{Formula 2}$$

In this regard, since the volume ($V_{N2}$) of nitrogen in the airbag 30 of Equation 2 must be the same as the volume ($V_{N2}$) of nitrogen in the lung of Equation 1, the FRC of Equation 3 is calculated using Equations 1 and 2.

$$FRC = F_{N2} V_B / 0.79 \qquad \text{Formula 3}$$

However, the concentration of nitrogen must be measured using a nitrogen concentration analyzer during the $N_2$ wash-out test. The nitrogen concentration analyzer has disadvantages of a high price, noise, and additional use of a large-sized vacuum pump, and thus, its usage is complicated. Accordingly, it is impossible to conduct the $N_2$ wash-out test to evaluate the FRC except in a large hospital.

SUMMARY OF THE INVENTION

Accordingly, the present invention has been made keeping in mind the above problems occurring in the prior art, and an object of the present invention is to provide a method of measuring an absolute lung volume based on $O_2/CO_2$ gas analysis. In the method, concentrations of oxygen and carbon dioxide in expired gas are measured using a relatively low-priced and general $O_2/CO_2$ analyzer, and a concentration of nitrogen is indirectly calculated using the measured concentrations of oxygen and carbon dioxide to determine precisely FRC. Additionally, in the method, measurement is simply conducted and a measurement device is low-priced.

In order to accomplish the above object, the present invention provides a method of measuring an absolute lung volume. The method comprises connecting an one-way valve 120 to a subject so as to separate an inspiration path 112 from an expiration path 114; measuring a flow rate (F) of respiratory gas using a flow sensor 130, which is provided in the expiration path 114; continuously measuring a concentration ($F_{O2}$) of oxygen and a concentration ($F_{CO2}$) of carbon dioxide using $O_2$ and $CO_2$ sensors 150 provided in the expiration path 114; correcting dynamic characteristics of the concentration ($F_{O2}$) of oxygen and the concentration ($F_{CO2}$) of carbon dioxide so that the dynamic characteristics agree with each other in terms of time; and analyzing oxygen and carbon dioxide gases using the following Equation.

$$FRC = \frac{1}{0.79} \int (1 - (F_{O2} + F_{CO2})) F \, dt$$

BRIEF DESCRIPTION OF THE DRAWINGS

The above and other objects, features and advantages of the present invention will be more clearly understood from the following detailed description taken in conjunction with the accompanying drawings, in which.

DESCRIPTION OF THE PREFERRED EMBODIMENTS

Hereinafter, embodiments of the present invention will be described in detail with reference to the drawings.

Figure 1:
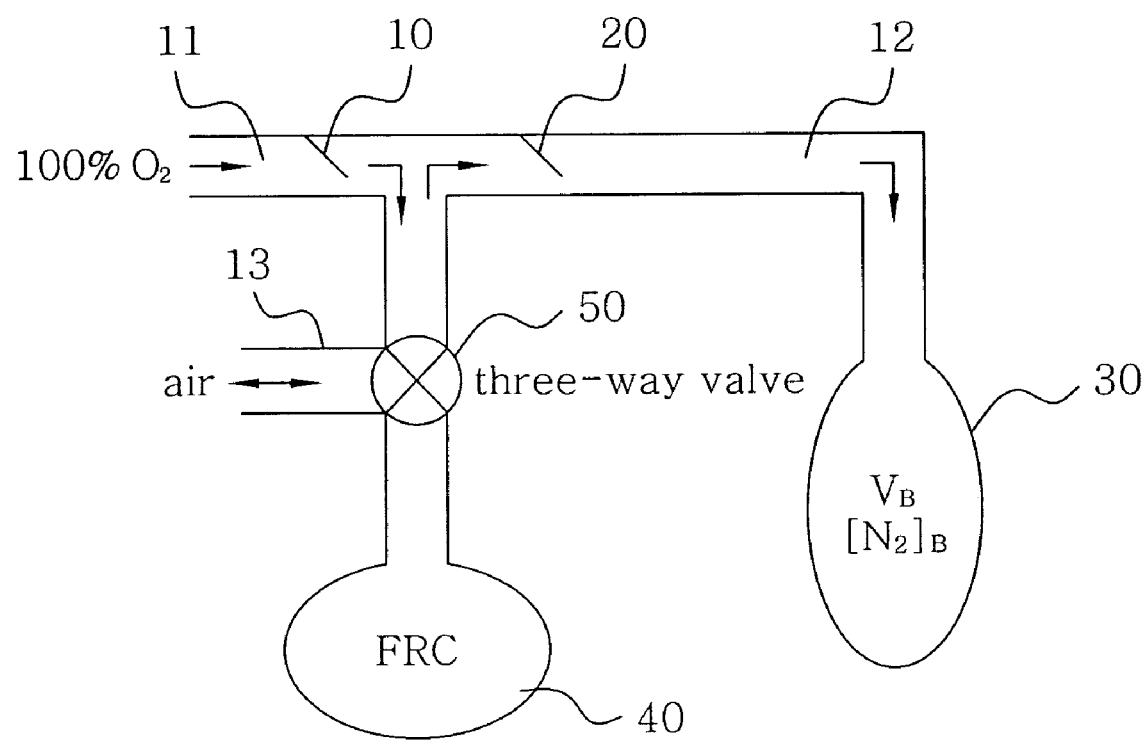
FIG. 1 illustrates a conventional $N_2$ wash-out test of measuring an absolute lung volume.
Figure 2:
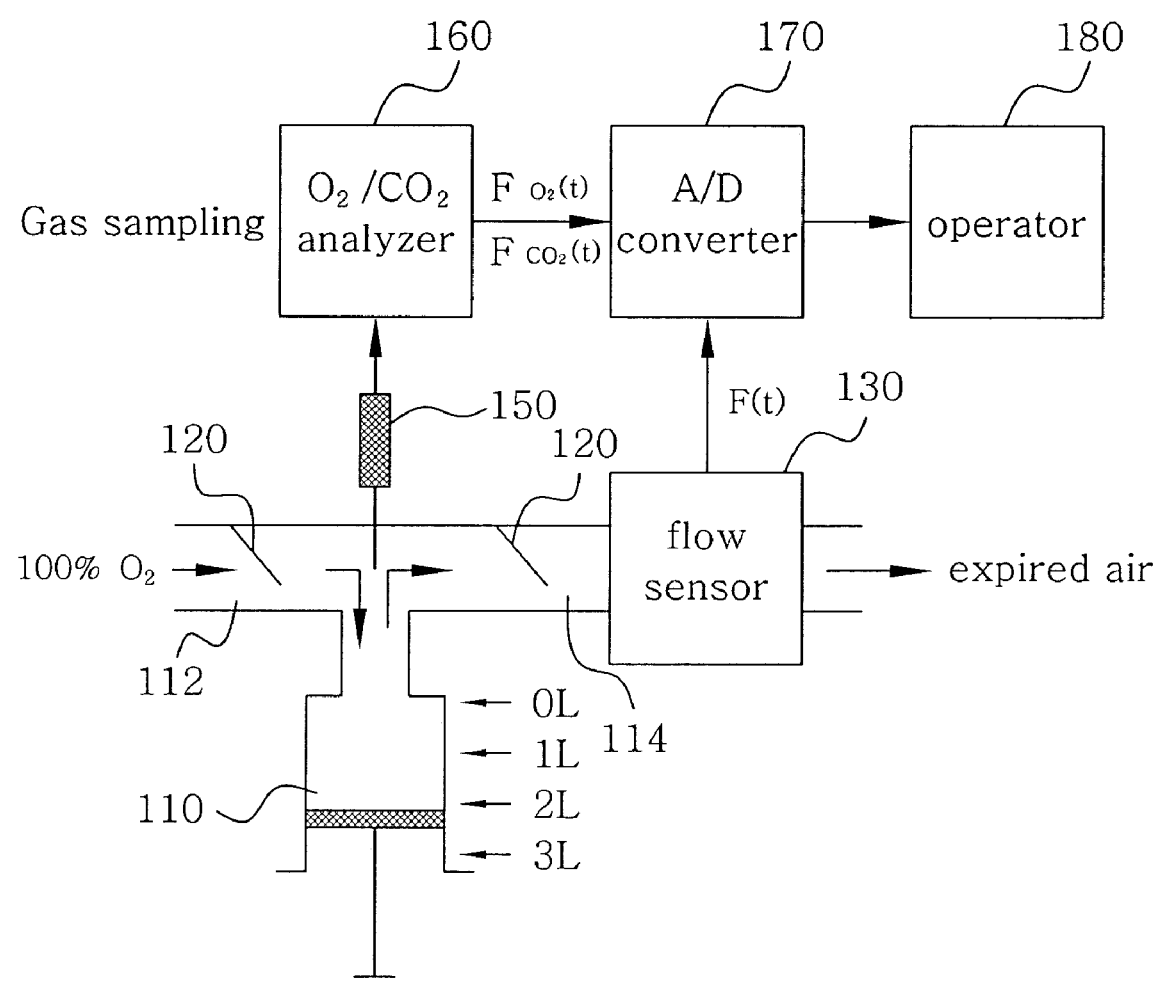
FIG. 2 illustrates a method of measuring an absolute lung volume based on $O_2/CO_2$ gas analysis according to the present invention.
Figure 3:
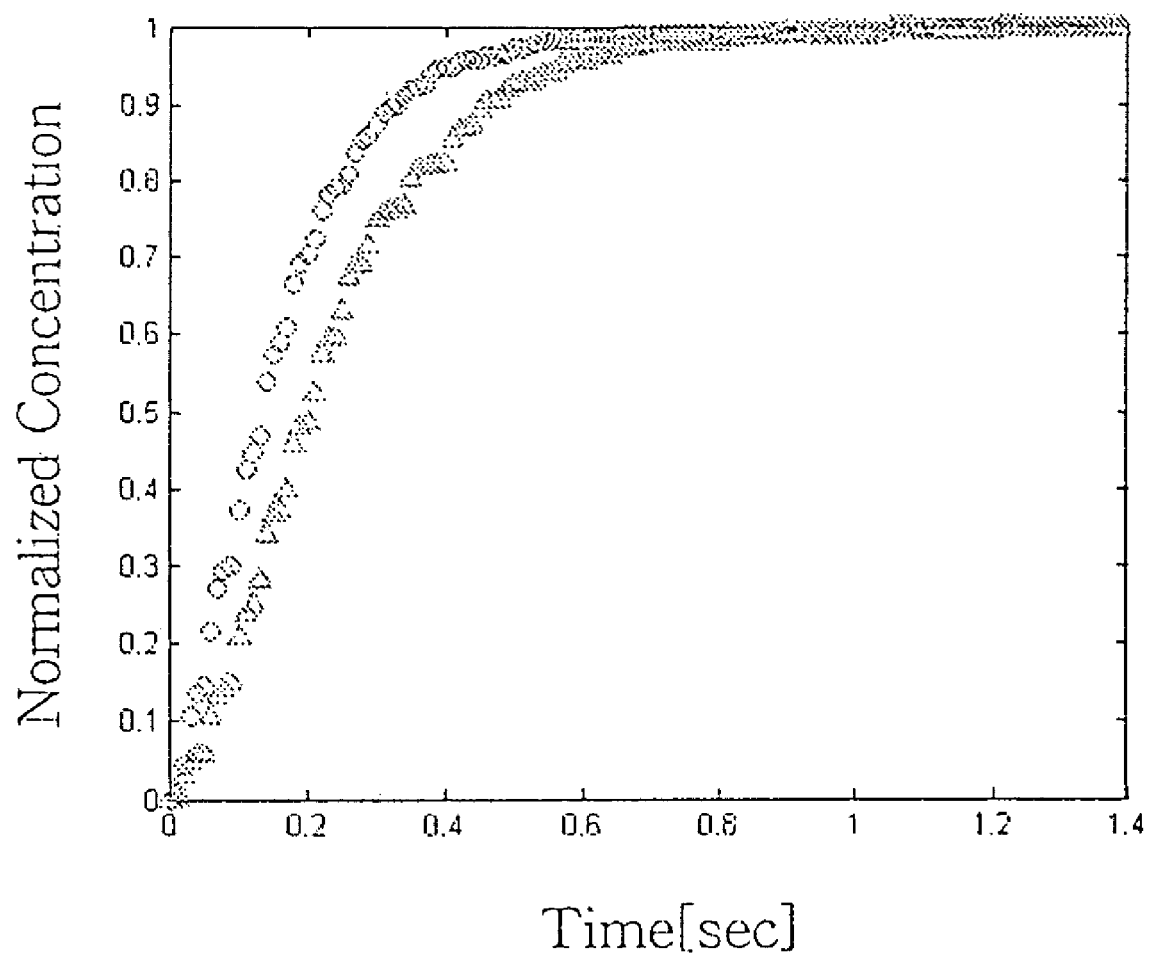
FIG. 3 is a graph showing response characteristics of an $O_2$ sensor and a $CO_2$ sensor used in the present invention.

Of the drawings, FIG. 2 illustrates a method of measuring an absolute lung volume based on $O_2/CO_2$ gas analysis according to the present invention, and FIG. 3 is a graph showing response characteristics of an $O_2$ sensor and a $CO_2$ sensor used in the present invention.

Figure 4:
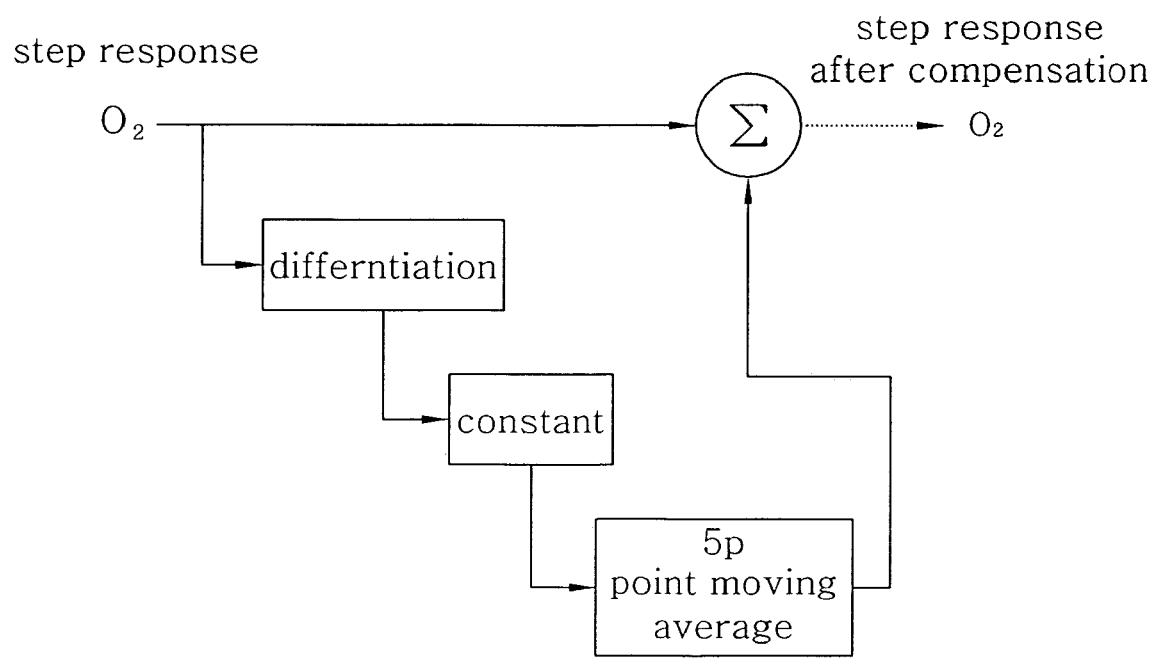
FIG. 4 is a block diagram showing compensation of output of the $O_2$ sensor used in the present invention.
Figure 5:
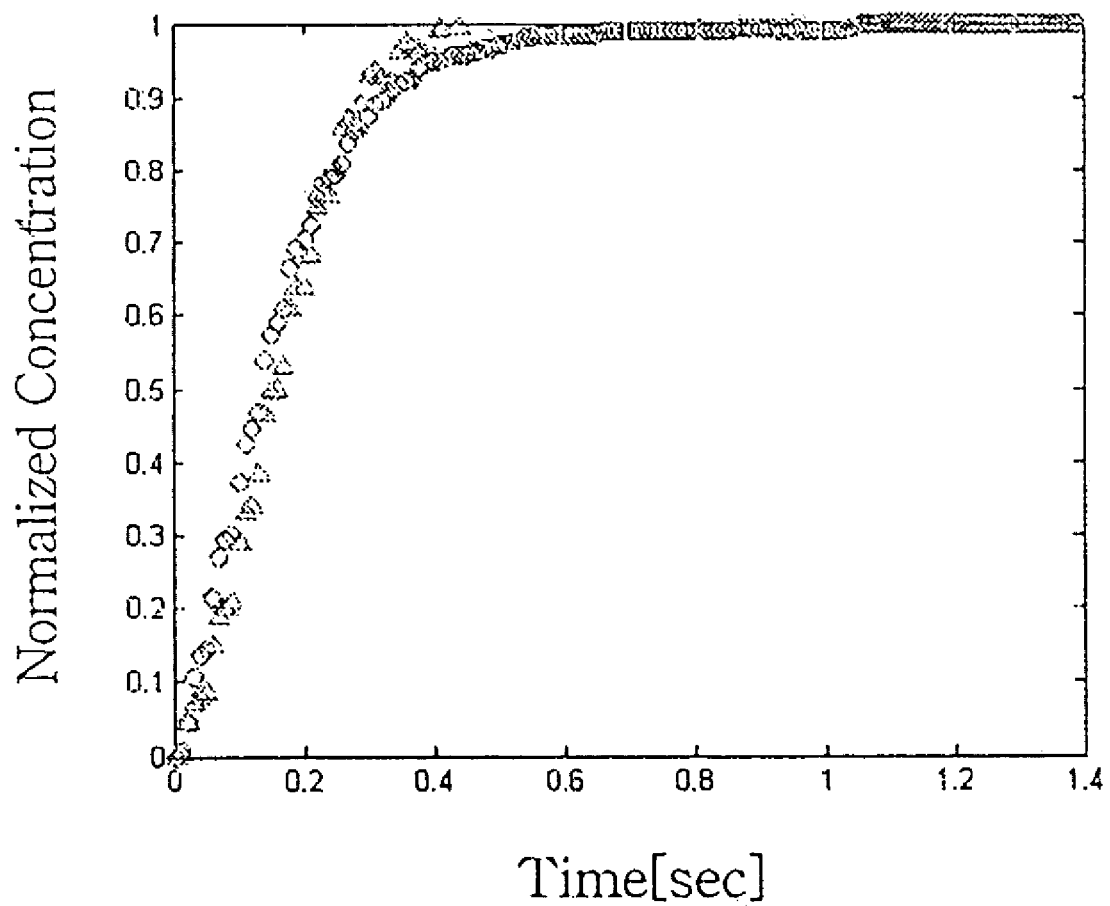
FIG. 5 is a graph showing response characteristics of the $O_2$ sensor and the $CO_2$ sensor after the compensation of the output of the $O_2$ sensor according to a procedure of FIG. 4.
Figure 6A:
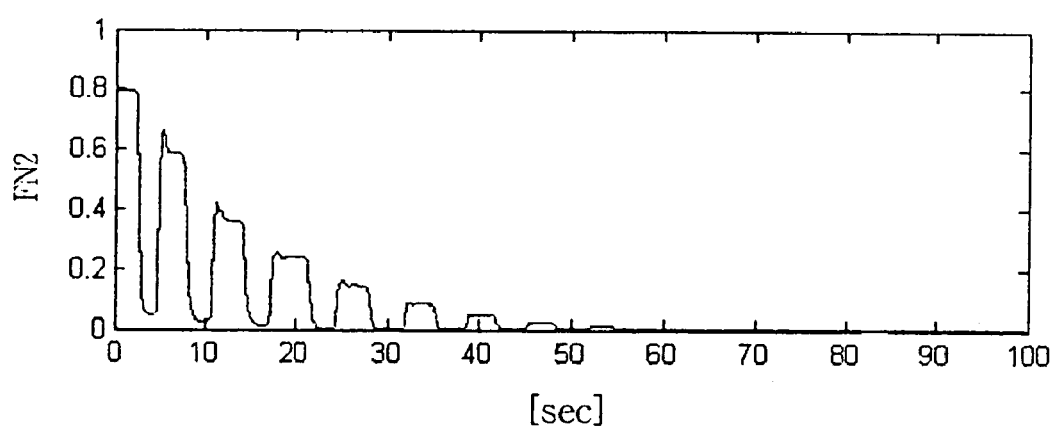
FIG. 6a is a graph showing a concentration of nitrogen gas which is calculated using concentrations of oxygen ($F_{O2}$) and carbon dioxide ($F_{CO2}$) and a flow rate (F) of respiratory gas according to the present invention.
Figure 6B:
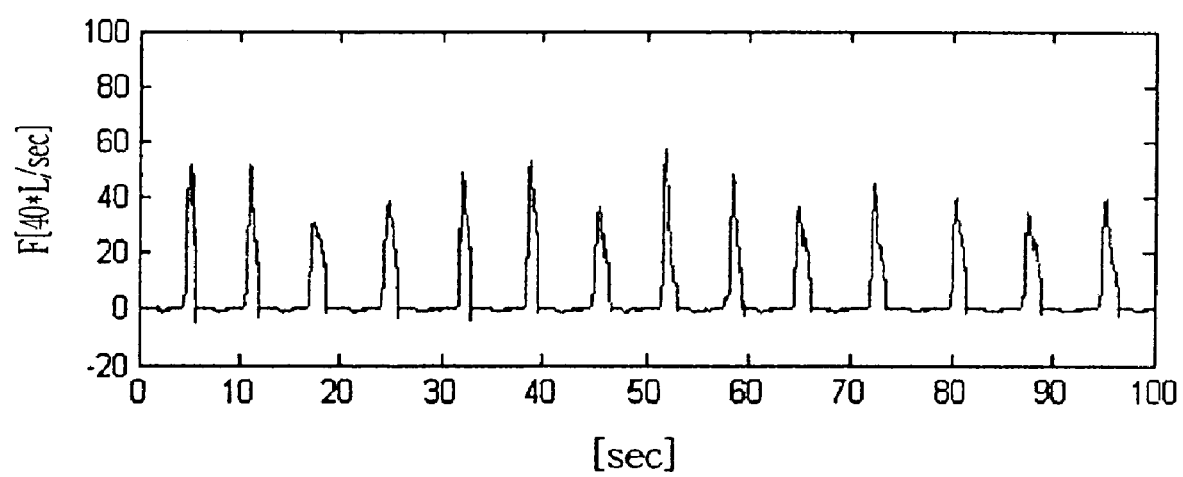
FIG. 6b is a graph showing output of an expiratory flow sensor according to the present invention.

FIG. 4 is a block diagram showing compensation of output of the $O_2$ sensor used in the present invention, and FIG. 5 is a graph showing response characteristics of the $O_2$ sensor and the $CO_2$ sensor after the compensation of the output of the $O_2$ sensor according to a procedure of FIG. 4. Additionally, FIG. 6a is a graph showing a concentration of nitrogen gas which is calculated using concentrations of oxygen ($F_{O2}$) and carbon dioxide ($F_{CO2}$) and a flow rate (F) of respiratory gas according to the present invention, and FIG. 6b is a graph showing output of an expiratory flow sensor according to the present invention.

In the method of measuring the absolute lung volume according to the present invention, respiratory gas expired by humans consists of only nitrogen ($N_2$), oxygen ($O_2$), and carbon dioxide ($CO_2$). Accordingly, if the total of concentration ratios of the above gases is 1 (=100%), Equation 3, by which a concentration of nitrogen ($N_2$) is measured to calculate an FRC of a subject, is transformed into the following Equation 4.

$$FRC = \frac{1}{0.79} \int (1 - (F_{O2} + F_{CO2}))Fdt \qquad \text{Equation 5}$$

In Equation 4, $F_{O2}$ and $F_{CO2}$ are concentration ratios of oxygen and carbon dioxide, respectively, and concentrations of oxygen and carbon dioxide may be measured using a general $O_2/CO_2$ analyzer which is frequently used to evaluate exercise functions or in metabolic monitoring and is relatively low-priced.

Furthermore, when a flow sensor is connected to an expiration path to detect a flow in the expiration path and the concentrations of oxygen ($F_{O2}$) and carbon dioxide ($F_{CO2}$) are continuously measured using the $O_2/CO_2$ analyzer, Equation 4 is transformed into the following integral Equation 5.

$$FRC = \frac{1}{0.79} \int (1 - (F_{O2} - F_{CO2}))Fdt \qquad \text{Equation 5}$$

Wherein, F is a flow rate of respiratory gas measured by the flow sensor. From Equation 5, it can be seen that since the concentration ($F_{O2}$) of oxygen, the concentration ($F_{CO2}$) of carbon dioxide, and the flow rate (F) of the respiratory gas are a continuous function of time, it is possible to calculate the FRC without measurement of the concentration of nitrogen ($N_2$).

In FIG. 2, a device for measuring the concentrations of oxygen and carbon dioxide to indirectly measure a temperature of nitrogen according to the present invention is illustrated. The device employs a 3 L syringe 110, which is a standard measuring device of the American Thoracic Society, instead of the lung of a subject who inspires air. One-way valves 120 are connected to an upper part of the syringe 110 to form an inspiration path 112 and an expiration path 114. A flow sensor 130, which is capable of continuously measuring a flow, is provided to the expiration path 114 to measure a flow rate (F) of respiratory gas.

As well, $O_2$ and $CO_2$ sensors 150 are provided between the one-way valves 120 to measure the concentrations of oxygen and carbon dioxide, and an $O_2/CO_2$ analyzer 160 is provided at output portions of the $O_2$ and $CO_2$ sensors 150 so as to continuously measure the concentration ($F_{O2}$) of oxygen and the concentration ($F_{CO2}$) of carbon dioxide using output signals of the $O_2$ and $CO_2$ sensors 150. An A/D converter 170 is provided at an output portion of the $O_2/CO_2$ analyzer 160 so as to convert analog signals with respect to the concentrations ($F_{O2}$, $F_{CO2}$) of oxygen and carbon dioxide and the flow rate (F) of respiratory gas, which is measured by the flow sensor 130, into digital signals. An operator 180 is provided at an output portion of the A/D converter 170 to calculate the absolute lung volume using the concentrations ($F_{O2}$, $F_{CO2}$) of oxygen and carbon dioxide and the flow rate (F) of the respiratory gas.

In a method of measuring the concentrations of oxygen and carbon dioxide to indirectly measure the concentration of nitrogen according to the present invention, a plunger of the 3 L syringe 110 containing air is repeatedly pulled and pushed predetermined times for a predetermined time to simulate respiration by the lung of the subject. In other words, inspiration starts to be conducted when a rubber bulb of the syringe is located at any one of 0, 1, and 2 L in an initial stage. Subsequently, inspiration and expiration are alternately repeated 10-15 times for 2 min using air, having a volume of 1 L, to simulate respiration by the lung of the subject.

During respiration, the signals output from the $O_2$ and $CO_2$ sensors 150 are analyzed using the $O_2/CO_2$ analyzer 160 to continuously measure the concentrations ($F_{O2}$, $F_{CO2}$) of oxygen and carbon dioxide. Furthermore, the flow rate (F) of the respiratory gas is measured using the flow sensor 130 provided at the expiration path 114.

At this stage, the operator 18 serves to compensate for oxygen measurements that have relatively slow measurement characteristics among outputs of the $O_2$ and $CO_2$ sensors, which have different measurement characteristics due to different operation mechanisms, so that the measurement characteristics of the oxygen measurements are the same as those of carbon dioxide measurements. In other words, the $O_2$ sensor and the $CO_2$ sensor have different delay times and the same time constant. However, as shown in FIG. 3, when a step response of gas fed into the $O_2/CO_2$ analyzer 160 is measured, response characteristics of the $O_2$ sensor are slower than those of the $CO_2$ sensor. Accordingly, as shown in FIG. 4, step response signals of the $O_2$ sensor are properly shifted on a time axis so as to agree with step response signals of the $CO_2$ sensor in terms of time. The step response signals of the $O_2$ sensor are differentiated to extract rapidly changed high frequency components among output signals of the $O_2$ sensor, and the components are multiplied by proper gain constants (K). A 5 point moving average of the output signals, which are multiplied by the gain constants, is performed to remove noise, and the resulting values are added to an initial step response signal of the $O_2$ sensor, thereby producing high frequency compensation signals.

With respect to this, the step response signals of the $CO_2$ sensor are subtracted from the step response signals of the $O_2$ sensor compensated according to the procedure of FIG. 4, and the resulting signal values are squared. The squared values are integrated, and a square root of an average value of the integrated values is extracted to produce a root-means-square (RMS) error. When the RMS error is minimized, the gain constant (K) is determined as an optimum value.

When the output of the $O_2$ sensor, compensated as described above, is compared to the output of the $CO_2$ sensor, the outputs of the two sensors are almost the same as each other as shown in FIG. 5. In other words, as shown in FIG. 3, the time constants of the step response signals of the output of the $O_2$ sensor before the compensation is conducted, and the output of the $CO_2$ sensor are 0.27 sec (oxygen) and 0.19 sec (carbon dioxide). Hence, the step response signal of the $O_2$ sensor is slower by 0.08 sec. However, if the step response signal of the $O_2$ sensor is compensated through the procedure of FIG. 4, the step response signals of the outputs of the $O_2$ sensor and the $CO_2$ sensor agree with each other in terms of time.

Therefore, when the output of the $O_2$ sensor is compensated so that the step response signals of the outputs of the $O_2$ sensor and the $CO_2$ sensor agree with each other in terms of time, and when a time axis is shifted so that delay times of the outputs of the $O_2$ sensor and the $CO_2$ sensor agree with a flow rate signal (F) of the respiratory gas, which is measured by the flow sensor 130 provided at the expiration path 114, the flow rate (F) of the respiratory gas, the concentration ($F_{O2}$) of oxygen, and the concentration ($F_{CO2}$) of carbon dioxide agree with each other in terms of time. Thereby, it is possible to gain the FRC using Equation 5 without the concentration measurement of nitrogen ($N_2$).

FIG. 6a is a graph showing a concentration ($F_{N2}$) of nitrogen, which is calculated using concentrations of oxygen ($F_{O2}$) and carbon dioxide ($F_{CO2}$), when a volume of air contained in the 3 L syringe 110 is 1 L in the device of FIG. 2, and FIG. 6b is a graph showing output of the flow sensor 130. In other words, since an expired flow consists only of oxygen, carbon dioxide, and nitrogen, the concentration ($F_{N2}$) of nitrogen is 1−(the concentration ($F_{O2}$) of oxygen+ the concentration ($F_{CO2}$) of carbon dioxide). With respect to this, from FIG. 6a, it can be seen that the concentration decreases in accordance with repetition of the respiration. Furthermore, from FIG. 6b, it can be seen that since the flow sensor 130 measures only the expired flow, the output of the flow sensor 130 is 0 during an inspiration process.

Furthermore, when the concentration of nitrogen, which is indirectly gained using the concentration ($F_{O2}$) of oxygen and the concentration ($F_{CO2}$) of carbon dioxide according to the present invention, is compared to the concentration of nitrogen, which is directly measured using a nitrogen analyzer, a correlation coefficient between the two results is 0.9984, and thus, the two results are very close to each other.

As described above, a method of measuring an absolute lung volume based on $O_2/CO_2$ gas analysis according to the present invention is advantageous in that a FRC is measured using an $O_2/CO_2$ analyzer, which is relatively low-priced and easily handled, instead of a nitrogen analyzer, which is costly and troublesome in use, thereby easily measuring the FRC that is clinically important, resulting in an improved quality of a medical examination.

The preferred embodiments of the present invention have been described in an illustrative manner with reference to the accompanying drawings, and it is to be understood that the terminology used is intended to be in the nature of description rather than of limitation. Many modifications and variations of the present invention are possible in light of the above teachings. Therefore, it is to be understood that within the scope of the appended claims, the invention may be practiced other than as specifically described.

What is claimed is:

1. A method of measuring an absolute lung volume, comprising:

connecting a one-way valve to a subject so as to separate an inspiration path from an expiration path;

measuring a flow rate of respiratory gas using a flow sensor, which is provided in the expiration path;

continuously measuring a concentration ($FO_2$) of oxygen and a concentration ($F_{CO2}$) of carbon dioxide using $O_2$ and $CO_2$ sensors provided in the expiration path;

correcting dynamic characteristics of the concentration ($F_{O2}$) of oxygen and the concentration ($F_{CO2}$) of carbon dioxide so that the dynamic characteristics agree with each other in terms of time; and analyzing oxygen and carbon dioxide gases using a following Equation $$FRC = \frac{1}{0.79} \int (1 - (F_{02} + F_{C02}))F dt$$

(wherein, the FRC is a functional residual capacity).

2. The method as set forth in claim 1, wherein step response signals output from the $O_2$ sensor are shifted on a time axis so as to agree with step response signals from the $CO_2$ sensor in terms of time, the shifted step response signals of the $O_2$ sensor are differentiated to extract rapidly changed high frequency components, the extracted components are multiplied by a predetermined gain constants (K), a 5 point moving average of output signals, which are multiplied by the gain constant (K), is performed to remove noise, and compensated signals having no noise are added to step response signals of the $O_2$ sensor, thereby achieving compensation.

3. The method as set forth in claim 2, wherein the step response signals of the $CO_2$ sensor are subtracted from the compensated step response signals of the $O_2$ sensor, the resulting signals are squared, the squared signals are integrated, a square root of an average value of the integrated signals is extracted to produce a root-means-square (RMS) error, and the gain constant (K) is a value when the RMS error is minimized.

4. The method as set forth in claim 1, wherein the concentration ($F_{O2}$) of oxygen and the concentration ($F_{CO2}$) of carbon dioxide are substituted into the following Equation so as to indirectly measure a concentration ($F_{N2}$) of nitrogen $$F_{N2}=1-(F_{O2}+F_{CO2}).$$

* * * * *